(12) United States Patent
Rich

(10) Patent No.: US 7,659,504 B1
(45) Date of Patent: Feb. 9, 2010

(54) OPTICAL SENSOR WITH AN OPTICAL ELEMENT TRANSMISSIVE TO WARMING RADIATION

(75) Inventor: David R. Rich, Glastonbury, CT (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

(21) Appl. No.: 11/429,343

(22) Filed: May 5, 2006

Related U.S. Application Data

(60) Provisional application No. 60/682,101, filed on May 18, 2005.

(51) Int. Cl.
*H01J 40/14* (2006.01)
(52) U.S. Cl. .................................................. 250/239
(58) Field of Classification Search .............. 250/226, 250/216, 239, 343, 345; 73/23.35, 23.4; 422/83, 84; 362/293
See application file for complete search history.

(56) References Cited

U.S. PATENT DOCUMENTS

| | | | |
|---|---|---|---|
| 4,315,186 A * | 2/1982 | Hirano et al. ............... 313/111 |
| 5,146,092 A | 9/1992 | Apperson et al. | |
| 5,212,707 A * | 5/1993 | Heidel et al. .............. 372/50.23 |
| 5,282,473 A * | 2/1994 | Braig et al. ................. 600/532 |
| 5,453,883 A * | 9/1995 | Chazallet .................... 359/890 |
| 5,793,044 A | 8/1998 | Mace et al. | |
| 6,100,952 A * | 8/2000 | Marvin et al. ................. 349/62 |
| 6,114,770 A * | 9/2000 | Akram et al. ............... 257/784 |
| 6,632,402 B2 | 10/2003 | Blazewicz et al. | |
| 6,655,855 B2 * | 12/2003 | Nakura et al. ................. 385/92 |
| 6,694,800 B2 * | 2/2004 | Weckstrom et al. ......... 73/25.01 |
| 7,372,209 B2 * | 5/2008 | Espiau et al. ................. 315/39 |

* cited by examiner

*Primary Examiner*—Georgia Y Epps
*Assistant Examiner*—Don Williams

(57) ABSTRACT

An optical gas sensor includes an optical element that is substantially transparent to both monitoring radiation and warming radiation. Such an optical element facilitates the removal of warming radiation from the optical gas sensor, thereby preventing an increase in the internal temperature of the sensor during use. Additionally, the warming radiation that is emitted from the optical gas sensor may be used to warm one or more windows of a sampling component that is configured for use with the sensor.

8 Claims, 7 Drawing Sheets

OPTICAL SENSOR WITH AN OPTICAL ELEMENT TRANSMISSIVE TO WARMING RADIATION

CROSS-REFERENCE TO RELATED APPLICATIONS

This application claims priority under 35 U.S.C. § 119(e) from provisional U.S. patent application No. 60/682,101 filed May 18, 2005 the contents of which are incorporated herein by reference.

BACKGROUND OF THE INVENTION

1. Field of the Invention

The present invention relates generally to optical sensors used in monitoring respiration, and, in particular, to optical sensors that include an optical element formed from a material, or combination of materials, that are substantially transparent to wavelengths of electromagnetic radiation that would otherwise cause warming of the optical element.

2. Background of Related Art

Optical sensors are useful for identifying and quantifying substances, including contaminants, that are present in a gas sample. Typically, an optical sensor includes a housing that contains a source of radiation, commonly referred to as an emitter, and a detector that receives radiation. The emitter provides one or more wavelengths of electromagnetic radiation that are passed through the gas sample, either directly or indirectly. The electromagnetic radiation is received by the detector and the signal from the detector facilitates evaluation of the gas sample, for example, for identifying and quantifying at least one constituent of the gas sample. In addition, the housing includes one or more optical elements, such as windows or lenses, through which the monitoring radiation is emitted into a sample and through which the monitoring radiation exits the sample.

Many optical gas sensors are configured to evaluate the direct affects of the sample on monitoring radiation or of the monitoring radiation on the sample. The emitter of such a sensor is typically configured to direct monitoring radiation into the sample. The detector of such a sensor senses a change in intensity of the monitoring radiation resulting from absorption of the monitoring radiation by one or more constituents of the sample, or senses temperature changes that occur as one or more constituents of the sample absorb the monitoring radiation. When correlated with a certain wavelength of monitoring radiation, the change in intensity or temperature indicates that a specific substance is present in the sample. The amount of the change in intensity or temperature corresponds to the amount of that substance in the sample.

Another type of optical gas sensor employs a technique known as "luminescence quenching." A luminescence quenching type sensor includes a luminescent material, e.g., a fluorescent or phosphorescent material, which is excited when exposed to monitoring radiation. When exposed to a certain substance, the intensity of luminescence of the luminescent material decreases, or is quenched. The degree to which the luminescence is quenched corresponds to the amount of the substance in the sample that causes the quenching.

The lenses and windows of optical gas sensors are typically fabricated from durable, scratch-resistant materials, such as sapphire. This is done to enable the optical elements to withstand the incidental contact to which the lenses or windows will inevitably be subjected during repeated use, cleaning, and storage.

FIG. 1 is a schematic representation of a portion of a conventional gas sensor 30 illustrating the opacity of a sapphire optical element 10, such as a window or lens, to wavelengths of warming radiation 20. While sapphire optical elements 10 have good transparency for visible light and near infrared wavelengths of electromagnetic radiation 22, which is typically referred to as "monitoring radiation", they absorb longer, warming wavelengths of infrared radiation 20, which is referred to herein as "warming radiation." The transparency of optical element 10 to monitoring radiation 22 is illustrated in FIG. 1 by showing the monitoring radiation passing through the window. The opacity of the optical element to warming radiation 20 is illustrated by showing the warming radiation as not passing through the optical element. For purposes of the present invention, "warming radiation" is radiation having a wavelength of at least about 6 µm.

Because conventional sapphire optical elements absorb warming radiation, a substantial portion of warming radiation 20 generated by an emitter of a sensor including such an optical element 10 is trapped by the optical element, thereby raising the internal temperature of the sensor to undesirably high levels. Optical gas sensors typically employ independent temperature control means to stabilize the temperature of their internal components. These undesirably high temperatures inside sensor 30 may interfere with such temperature control means, and affect the performance of sensor 30, degrading accuracy and long term durability.

While heating of an optical element can have undesirable consequences for an optical sensor, there are situations where absorption of warming radiation 20 has benefits. In respiratory monitoring, as well as when other gases and fluids are monitored, condensation, or "fogging," occurs when a relatively warm sample, such as an exhaled breath, contacts a colder object, such as the window or lens of a sampling component (typically referred to as a "cell" or "cuvette") of an optical monitoring system. Basically, as the portions of the sample that contact the window of the sampling component are cooled, water molecules in the form of vapor condense, fogging the window. Unfortunately, condensation, or fog, on components of the optical monitoring system can interfere with the monitoring process and adversely affect on the accuracy of the data that may be obtained with such systems. Absorption of warming radiation results in heating of the window, thereby reducing fogging, much like the defrost feature in an automobile heater.

The problem of condensation on the windows of optical monitoring components has also been addressed by various other approaches. One approach to reducing or eliminate fogging on the windows of sampling components involves de-humidifying the sample with a desiccating material, such as NAFION®. However, the inclusion of a de-humidifier in an optical gas sensor increases the complexity and cost of the sensor.

Other approaches have been used to heat the windows of the gas sensor directly. An example of such a conventional window-heating technique includes the use of an electrical heater to warm each window of a sampling component. Of course, power must be supplied to an electrical heater for it to work. Thus, additional circuitry must be added to the system, increasing the overall complexity and cost of a system that includes an electrical heater.

SUMMARY OF THE INVENTION

Accordingly, it is an object of the present invention to provide an optical sensor that overcomes the shortcomings of conventional optical sensors. This object is achieved according to one embodiment of the present invention by providing an optical sensor that includes a housing, a radiation emitter disposed within the housing, and an optical element through which the radiation is emitted. The optical element is at least partially transparent to at least one warming wavelength of electromagnetic radiation. The present invention includes windows, lenses, and other optical elements for use in optical sensors. For the sake of simplicity, the term "optical element" is defined herein to include windows, lenses, and other electromagnetic radiation-transmissive optical components.

An optical element according to the present invention is substantially transparent, i.e., has a desirable level of transmissivity, to one or more wavelengths of electromagnetic radiation to be used in evaluating the constituents of a sample, i.e., monitoring radiation. Additionally, an optical element of the present invention permits electromagnetic radiation warming wavelengths of electromagnetic radiation, e.g., about 6 μm to about 10 μm, to pass therethrough, or is at least partially transparent to such "warming radiation."

In another aspect, the present invention includes an optical element that has an acceptable level of transparence to the wavelengths of monitoring radiation that will be directed therethrough, but have regions that absorb a substantial portion of the warming radiation directed therethrough. These warming radiation-absorbing regions are configured or positioned to absorb enough warming radiation to heat the optical element to a suitable, condensation preventing temperature, such as about 20° C. or greater. The warming radiation-absorbing regions may be positioned at least partially over an optical pathway through the window.

In addition to optical elements, the present invention relates to components of optical sensing systems, as well as to optical sensing methods. By way of nonlimiting example, the present invention includes components of respiratory gas sensors, including sampling components, e.g., airway adapters, cuvettes or cells, etc, and transducers, which house the emitters and detectors of an optical sensor.

Systems that include one or more components with an optical element that is substantially transparent to a warming wavelength of radiation are also within the scope of the present invention. When used in optical gas sensing systems, an optical element that incorporate teachings of the present invention allow warming radiation to escape the sensor and warm the windows of a sampling component, such as a cuvette.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 2:
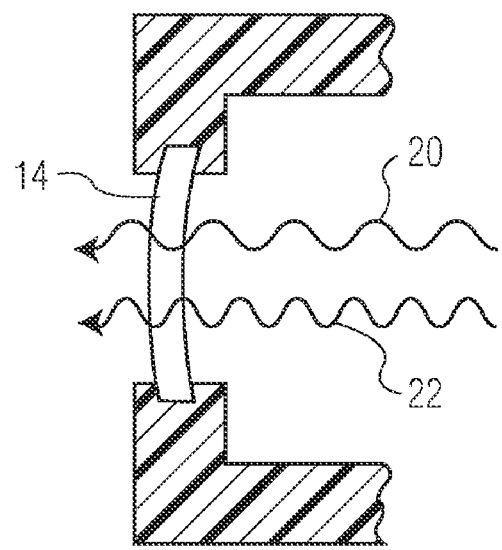
FIG. 2 is a schematic representation of a portion of an optical element that is substantially transparent to warming wavelengths of radiation.
Figure 3:
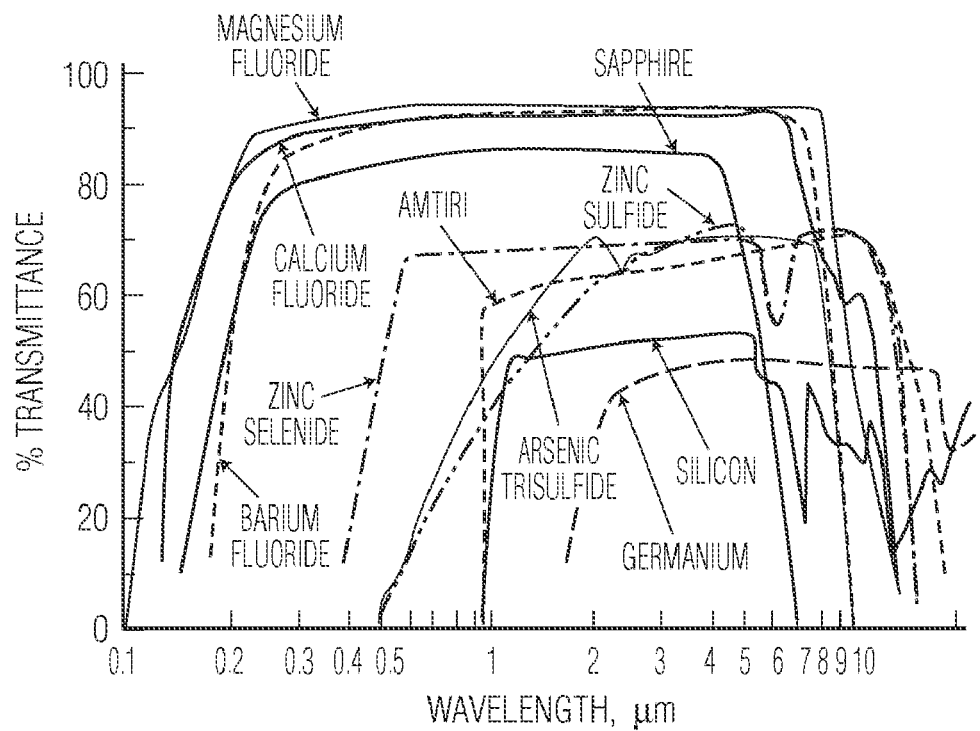
FIG. 3 is a graph showing the spectral transmittances of different materials to infrared radiation of different wavelengths.

FIG. 2 illustrates a first embodiment of an optical element 14 that incorporates the teachings of the present invention. Optical element 14 formed from a material that is substantially transparent (e.g., have a transmittance of about 70%, about 80%, about 90%, or greater) to warming radiation 20 and, thus, permits a significant percentage of warming radiation 20 to pass therethrough. Of course, optical elements that are formed from materials that are less transparent (e.g., having a transmittance of about 60%, about 50%, about 40%, about 30%, about 20%, or less) to warming radiation 20 are also within the scope of the present invention. As optical element 14 is configured for use in an optical sensor, it is also sufficiently transparent to each wavelength of monitoring radiation that will be directed therethrough to effect evaluation of a sample. Examples of materials that are suitable for use in forming optical element 14 include, without limitation, silicon, barium fluoride, germanium, potassium chloride, zinc selenide, calcium fluoride ($CaF_2$), magnesium fluoride ($MgF_2$), and other materials with similar transmittance properties, including, but not limited to those shown in FIG. 3. The transmittances of some of the foregoing materials to warming radiation 20 are shown in FIG. 3.

Optical element 14 may be formed by processes that are known in the art, such as a mask and etch processes, molding, machining, or grinding, etc., as well as optional polishing, and suitable for use with the material of choice in forming an optical element having the desired physical dimensions and features.

Figure 1:
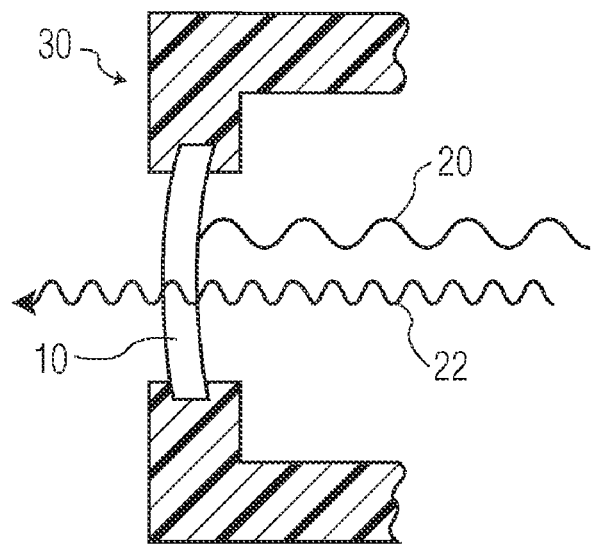
FIG. 1 is a schematic illustration of a portion of an optical sensor using a conventional sapphire optical element that does not transmit wavelengths of warming radiation.

The following EXAMPLE compares the heat absorption of a conventional sapphire optical element 10 (FIG. 1) to a silicon optical element 14 (FIG. 2).

EXAMPLE

In this example, CAPNOSTAT® III capnographs, which are also referred to herein as "transducers" and "sensors", available from Respironics, Inc., of Murrysville, Pa., were used to evaluate both a 0.240 inch diameter sapphire hemispherical lens and a 0.240 inch diameter silicon hemispherical lens. The sapphire lens is a standard feature of the CAPNOSTAT® III capnograph. This testing was performed with four different Capnostats.

A Fluke model 50D digital thermometer with 40 AWG "K" type thermocouples, available from Fluke Corporation of Everett, Wash., was used to measure the temperature of both lenses. The results are set forth in the following TABLE:

TABLE

| Capnostat # | Sapphire Lens Temperature | Silicon Lens Temperature |
| --- | --- | --- |
| 1 | 96.5° C. | 72.1° C. |
| 2 | 96.3° C. | 68.0° C. |
| 3 | 95.4° C. | 68.7° C. |
| 4 | 98.7° C. | 71.5° C. |

As the results in the TABLE indicate, following thirty minutes of exposure to warming radiation, the sapphire lens absorbed significant amounts of warming radiation; enough to heat the lens by about 25° C. to about 30° C. more than the temperature of the silicon lens.

Exemplary alternative embodiments of optical elements 14a-14e, which includes windows, lenses, or any other optical component that incorporate the teachings of the present invention, are shown in FIGS. 4A-8B. Each optical element 14a-14e in these figures includes a base substrate 12 having the same characteristics as those described with reference to optical element 14 (FIG. 2). Namely, the base substrate is formed from a material that is substantially transparent to warming radiation. In each embodiment, however, a coating, which is indicated by reference numerals 18a-18e, covers of all of the optical element (FIGS. 8A and 8B) or covers all, or part, of a region 16 of base substrate 12. Region 16 corresponds to the portion of the base substrate that is located across an optical path of the sensing system of which the optical element is a part.

The coating used as coatings 18a-18e is formed from a material that absorbs a sufficient portion, e.g., at least about 30% or more, of warming radiation 20 (FIGS. 1 and 2) directed therethrough to warm the optical element to a desired temperature, e.g., about 20° C., about 37° C., etc. The coating used as coating 18a-18e may, by way of nonlimiting example, be formed from sapphire, a borosilicate glass (BK7), crystalline quartz, polycarbonate, or another material having similar optical properties, namely good transparence to visible light and near infrared wavelengths of electromagnetic radiation, and poor transparence to warming radiation. Optionally, part of region 16 of base substrate 12 may remain exposed laterally beyond such a material. Thus, the optical elements shown in these embodiments provides some degree of absorption of the warming radiation; the degree being controlled based on the pattern, shape, size, material, etc. used in the coating.

Figure 4A:
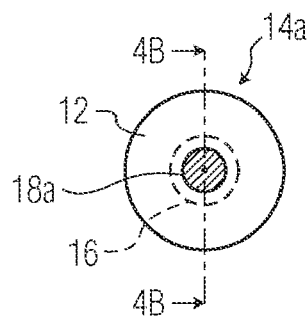
FIGS. 4A-7B illustrate exemplary embodiments of an optical element according to the principles of the present invention, which includes regions that absorb warming radiation and regions that transmit warming radiation.
Figure 4B:
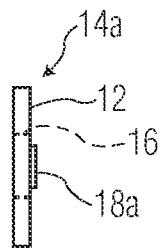

FIGS. 4A and 4B illustrate an optical element 14a having a coating 18a that appears as a small spot, or circle, that occupies a central location of region 16 of base substrate 12, but does not fully occupy region 16.

Figure 5A:
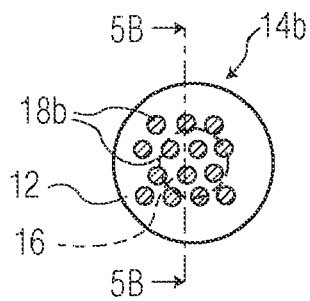
Figure 5B:
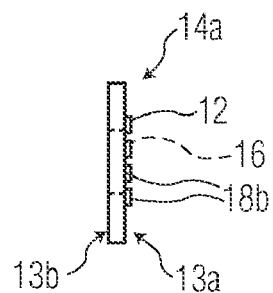

FIGS. 5A and 5B illustrate an optical element 10b having a coating 18b that comprises multiple, spaced apart spots arranged randomly, psuedorandomly, or in a selected pattern over at least a portion of at least one surface 13a or 13b of base substrate 12. Again, only a portion of region 16 of base substrate 12 is covered by coating 18b.

Figure 6A:
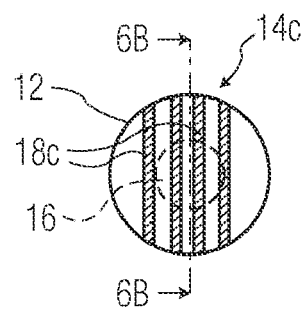
Figure 6B:
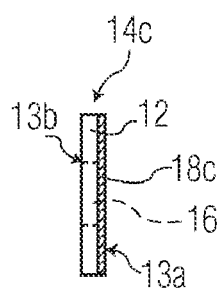

FIGS. 6A and 6B illustrate an optical element 14c having a coating 18c that includes multiple stripes or lines of warming radiation absorbing material. The stripes or lines of coating 18c cover a portion of region 16 of base substrate 12 on one or both surfaces 13a, 13b.

Figure 7A:
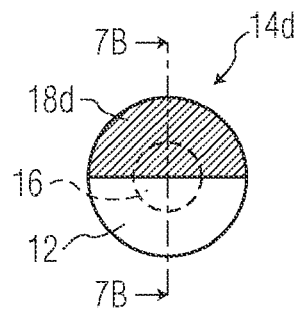
Figure 7B:
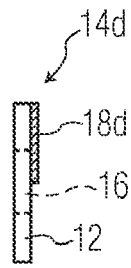

FIGS. 7A and 7B illustrate another variation of a coating 18d, which covers half of region 16 of base substrate 12.

Figure 8A:
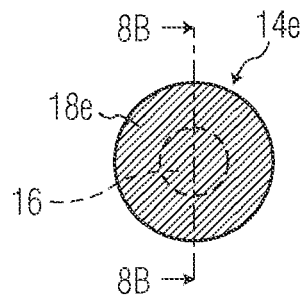
FIGS. 8A and 8B depict an embodiment of an optical element with a base substrate that is formed from a material that is transparent to warming radiation and a thin coating that is partially transparent to warming radiation.
Figure 8B:
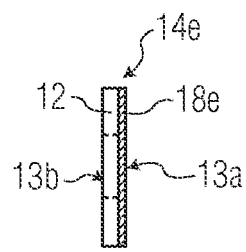

FIGS. 8A and 8B illustrate yet another alternative for an optical element 14e that includes a coating 18e covering at least one entire surface 13a, 13b of base substrate 12. Coating 18e is formed from a material that absorbs at least some warming radiation. As coating 18e covers substantially all of one or both surfaces 13a and 13b of base substrate 12, but permits at least some warming radiation 20 to pass therethrough, the thickness of coating 18e is tailored (e.g., made sufficiently thin) to provide the desired level of transmittance to warming radiation 20.

Base substrate 12 of the optical elements 14a-14e may be formed by any known or conventional processes, such as mask and etch processes, molding, machining, or grinding, etc., as well as optional polishing, suitable for use with the material of choice in forming base substrate 12. Coating 18a-18e may also be formed by known processes, such as blanket material deposition (such as physical vapor deposition (PVD) process, sputtering, chemical vapor deposition (CVD) process, atomic layer deposition (ALD), etc.), mask and etch processes, screen printing, and suitable curing processes to adhere preformed elements to base substrate 12. The techniques by which coating 18a-18e are formed depends, of course, upon the material that is used to form the coating, as well as the compatibility of such techniques with the material from which base substrate 12 is formed.

A similar effect may be achieved by doping, rather than coating, various areas of a base substrate 12. For example, areas of base substrate 12, such as those depicted in FIGS. 4A-7B as being covered with a coating 18a-18d, may be doped with a material that will render these areas substantially opaque to warming radiation. Examples of such materials include boron, when base substrate 12 comprises silicon or fused silica. Known processes, such as masking and chemical diffusion, ion implantation, etc., may be used to dope selected areas of a base substrate 12.

As an alternative to coating 18e, a low concentration of a dopant, such as boron, may be introduced throughout base substrate 12 by diffusion or implantation processes of any conventional process. The dopant concentration is tailored (e.g., sufficiently dilute) to provide a desired level of transmittance to warming radiation 20. Coating 18e may be fabricated by any known, suitable manner, such as by the techniques that have been described in reference to coatings 18a-18d.

Figure 9:
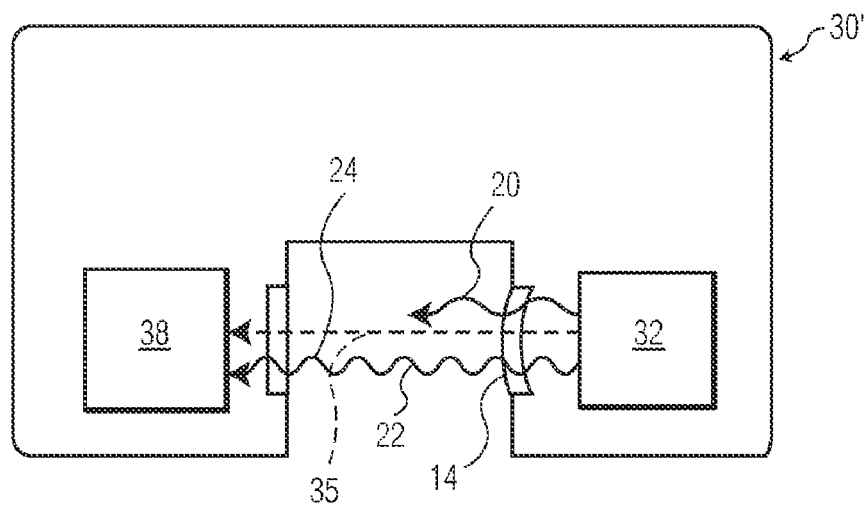
FIG. 9 illustrates an exemplary embodiment of an optical sensor including an optical element according to the principles of the present invention.

An example of an optical sensor 30' according to the present invention, which includes at least one optical element 14 (specifically, a lens), is shown in FIG. 9. As depicted, optical sensor 30' is a capnograph, which is a device that includes a radiation source 32 configured to introduce at least one wavelength of monitoring radiation 22 of a first intensity into a respiratory sample. Optical sensor 30' also includes a radiation detector 38 configured to detect a second intensity of the wavelength of infrared light that passes through the respiratory sample. Typically, the second intensity is less than the first intensity, or "attenuated," because the respiratory sample includes some carbon dioxide that absorbs the monitoring radiation 22 that has been introduced into the respiratory sample. Accordingly, the light that is ultimately sensed by detector 38 of optical sensor 30' and quantified is referred to herein as "attenuated radiation" 24.

Optical element 14 of optical sensor 30' is a lens through which at least one wavelength of infrared light is emitted from radiation source 32. After warming radiation 20 passes through optical element 14, it impinges upon other features within an optical path 35 of optical sensor 30'. Optical sensor 30' may be used in conjunction with any sampling component, such as a mainstream or side stream adapter, configured for use therewith, including sampling components of existing configurations. Alternatively, optical sensor 30' may be used with a sampling component that includes one or more optical elements 14a-14e (FIGS. 4A-8B) that incorporate the teachings of the present invention.

Figure 10:
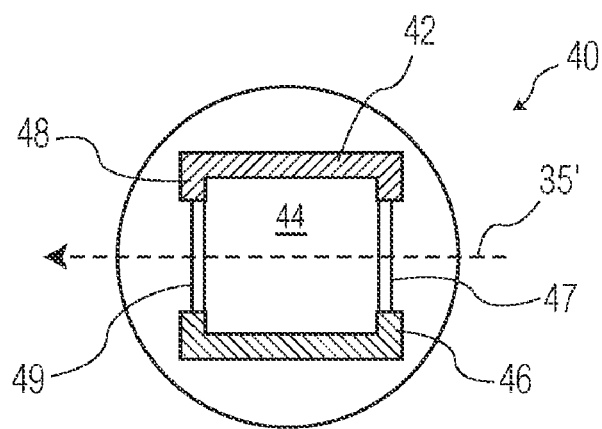
FIG. 10 is an exemplary embodiment of a sampling component adapted for use with the optical sensor of FIG. 9.

FIG. 10 is an exemplary illustration of such a sampling component 40 according to the principles of the present invention. Sampling component 40 includes a housing 42 within which a sample flow path 44, oriented transverse to the plane of the drawing sheet, is located. Housing 42 includes a source side 46 and a detection side 48, each of which includes a window 47 and 49, respectively, that is positioned along optical path 35' of when the sampling component is coupled to an optical sensor. As a result, monitoring radiation and, optionally, some warming radiation is introduced across sample flow path 44 (on source side 46) and exits the sampling component (on detection side 48). The present invention contemplates that window 47 on source side 46 corresponds to optical elements 14-14e discussed above. The present invention also contemplates that window 49 on detection side 48 comprises any optically suitable window, including, but not limited to, a conventional window 10, i.e., a window formed from sapphire, polycarbonate, etc., or a window that corresponds to optical elements 14-14e of the present invention.

Figure 11:
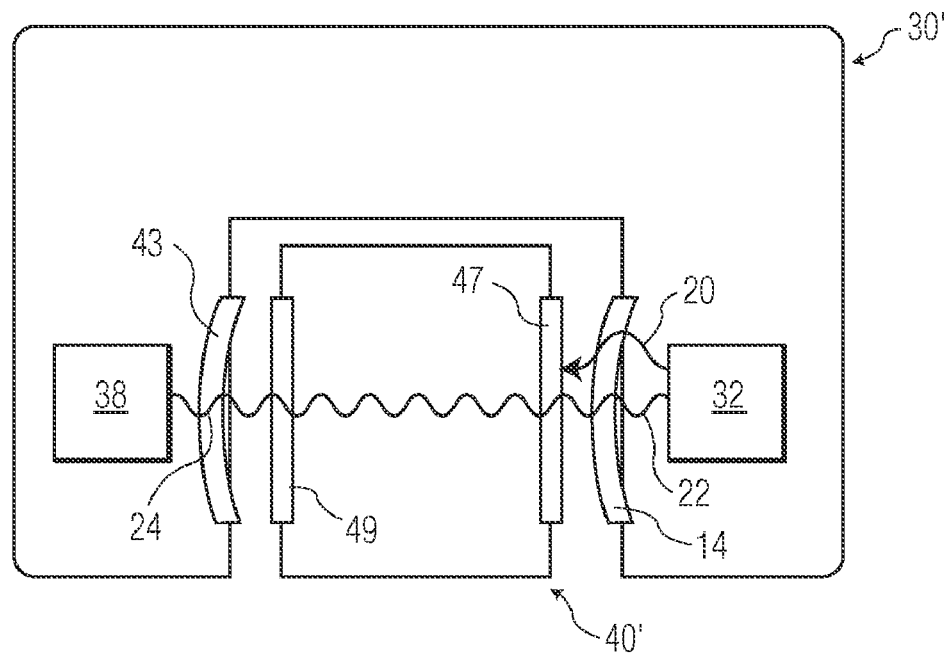
FIG. 11 is a schematic representation of one embodiment of a gas monitoring system including an optical sensor and a gas sampling component showing the transmittance of monitoring radiation and warming radiation through optical elements of the gas monitoring system.

FIG. 11 illustrates an optical sensor 30' and a sampling component 40' according to the principles of the present invention. In this embodiment, optical sensor 30' corresponds to the optical sensor of FIG. 9. Thus, optical sensor includes an optical element 14 that is substantially transmissive to warming radiation 20 emitted by source 32, so that the warming radiation passes to sampling component 40'. In this embodiment, window 47' of sampling component 40', which is located proximate to source 32 when the sampling component is assembled with the optical sensor, corresponds to a conventional optical element 10 that absorbs warming radiation 20 and passed monitoring radiation 22. Thus, a substantial amount of warming radiation 20 that passed through optical element 14 is directed toward window 47' and is absorbed by the window. This is illustrated in FIG. 11 by showing warming radiation 20 passing through optical element 14 and ending at window 47'.

Window 49' proximate to radiation detector 38 is a conventional optical element 10 or an optical element 14-14e of the present invention. Because most, if not all, of the warming radiation is absorbed by window 47' in this embodiment, it is largely irrelevant whether window 49' is transmissive to warming radiation. An optical element 43 is positioned on optical sensor 30' proximate to radiation detector 38 and is a conventional optical element 10 or an optical element 14-14e of the present invention.

Figure 12:
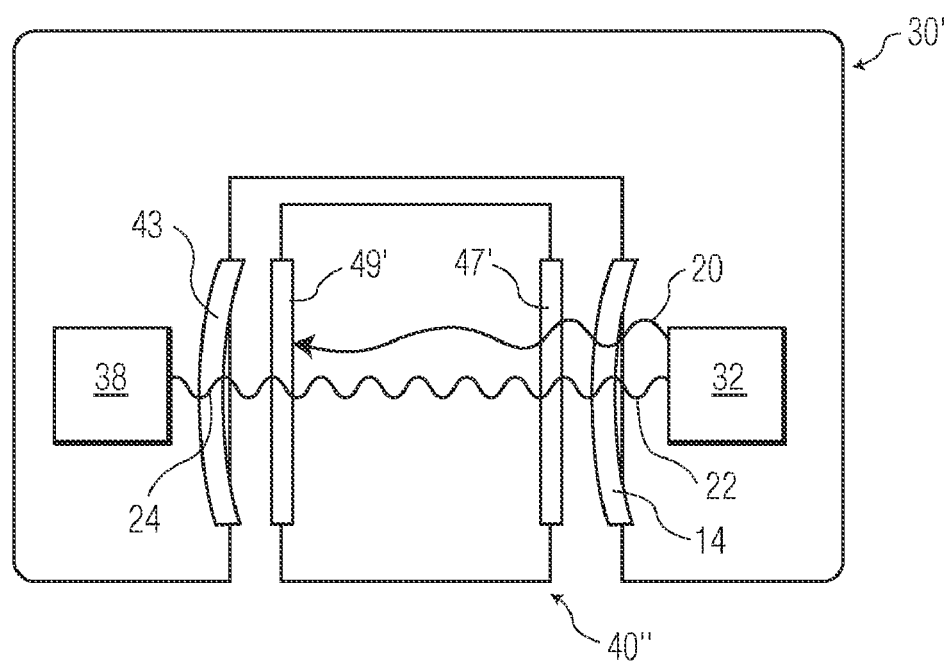
FIG. 12 is a schematic representation of a second embodiment of a gas monitoring system including an optical sensor and a gas sampling component showing the transmittance of monitoring radiation and warming radiation through optical elements of the gas monitoring system.

FIG. 12 illustrates an optical sensor 30' and a sampling component 40". Sampling component 40" is similar to the sampling component of FIG. 11, except for the configuration of window 47'. In this embodiment, window 47' corresponds to an optical element 14-14e so that it is at least partially transmissive to warming radiation. As a result, some warming radiation 20 is absorbed by window 47' and some warming radiation 20 passes through to window 49'. Window 49' is a conventional optical element 10 or an optical element 14-14e of the present invention. If both windows 47' and 49' of sampling component 40" permit some warming radiation 20 to pass therethrough, the present invention contemplates that warming radiation making its way back into optical sensor 30' is of a relatively low intensity so that it will not cause optical sensor 30' to heat to an undesirable temperature. In this embodiment, both windows 47' and 49' absorb at least some radiation so that both windows are heated to some extent. In an exemplary embodiment, the windows of the sampling component are heated enough by the absorption of warming radiation so as to reduce or eliminate fogging of these windows.

As FIGS. 11 and 12 illustrate, when an optical sensor 30' and a sampling component 40', 40" that incorporate teachings of the present invention are used together, warming radiation 20 is beneficially removed from optical sensor 30' and used to heat windows 47, 47', 49, 49' of sampling component 40', 40". Of course, the use of windows 47, 47', 49, 49' to facilitate the removal of heat from optical sensor 30' and to optionally heat the windows of the sampling component may accompany other heat removal (from a sensor) and optional heating (of windows of a sample component) techniques and apparatus.

Figure 13:
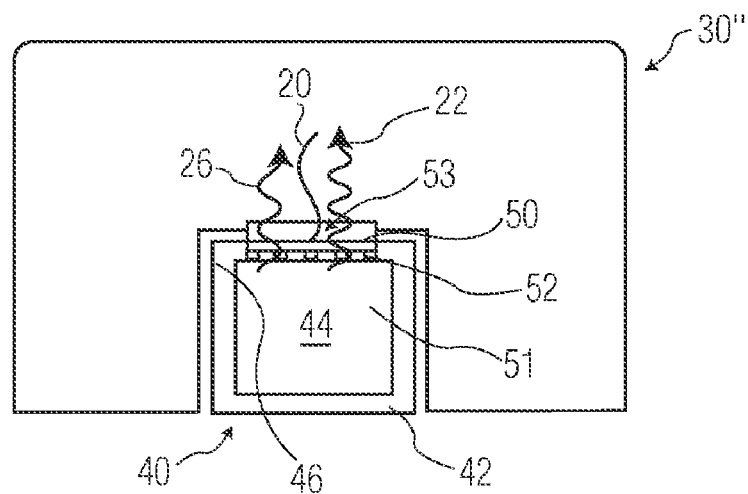
FIG. 13 depicts yet another exemplary embodiment of an optical sensor that includes a window according to the present invention.

FIG. 13 schematically depicts another embodiment of an optical sensor 30'" that incorporates teachings of the present invention. Optical sensor 30'" is configured for use in luminescence quenching monitoring techniques. It includes at least one optical element 53 through which monitoring radiation 22 and warming radiation 20 from a source (not shown) within optical sensor 30'" are emitted. Optical sensor 30'" also includes a detector (not shown), which is positioned so as to receive emitted radiation 26 that enters optical sensor 30'" through optical element 53.

Optical sensor 30'" is configured to be assembled with a known sampling component 40 that is configured for use employing luminescence quenching techniques to monitor one or more substances in a sample. Such a sampling component 40 includes a housing 42, a sample flow path 44 that extends through housing 42, which is oriented transverse to the plane of the drawing sheet, and a monitoring surface 46. A window 50 is located in monitoring surface 46 and includes an inner surface 51 exposed to sample flow path 44. Window 50 is formed from an optical grade material, such as polycarbonate, that will absorb warming radiation. A luminescent material 52 is secured to inner surface 51 of window 50.

When used with optical sensor 30'", warming radiation 20 from the radiation source of optical sensor 30'" passes through optical element 53 and is absorbed by window 50, which may then be heated by warming radiation 20 to a substantially constant temperature. Such warming of window 50 counteracts fluctuations or variations in the temperature of luminescent material 52, including the temperature increases that occur beginning with initial use of sampling component 40.

Other means for directing warming radiation from optical sensors are also within the scope of the present invention, including use of dichroic filters to separate warming radiation from monitoring radiation and associated optics to divert the warming radiation out of the sensor.

Figure 14:
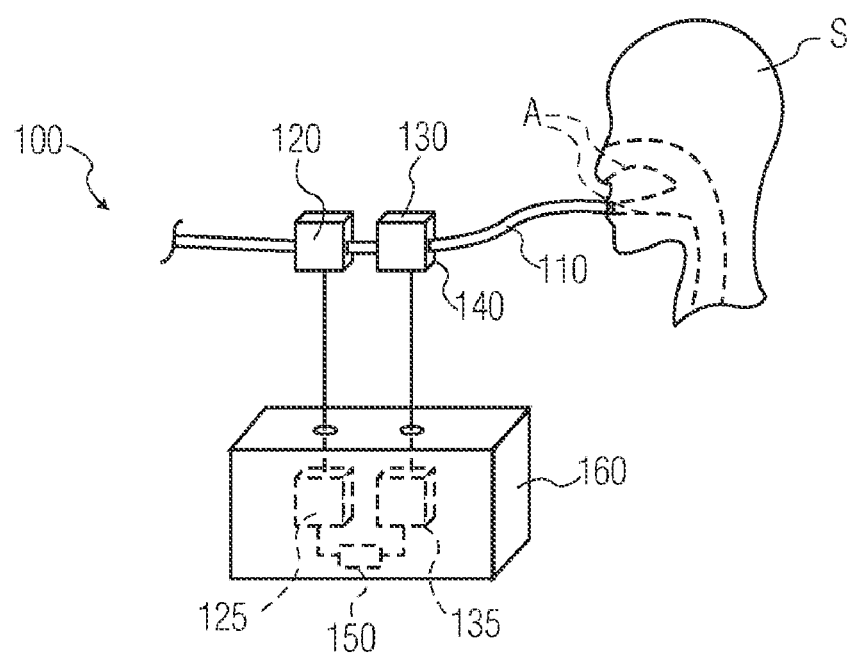
FIG. 14 is a schematic representation of a diagnostic system that includes at least one component with an optical element that is transparent to at least some wavelengths of warming radiation.

Turning now to FIG. 14, a schematic representation of a diagnostic system 100 incorporating the teachings of the present invention is illustrated. Diagnostic system 100 includes, among other things, a tubular airway 110, which is referred to as a patient circuit or breathing circuit, in communication with an airway A of a subject S. Diagnostic system 100 also includes an optical sensor 130 assembled with a sampling component 140 positioned along tubular airway 110. At least one of optical sensor 130 and sampling component 140 includes a warming radiation-transparent optical element (a lens, window, etc.).

Examples of other features that may be included in optical sensor 130, as well as specifics regarding the manner in which optical sensor communicates with other components of diagnostic system 100, are disclosed in U.S. Pat. Nos. 6,632,402; 5,793,044, and 5,146,092, the contents of each of which are hereby incorporated by this reference in their entireties.

Diagnostic system 100 may optionally include a flow meter 120 of a type known in the art. Optical sensor 130 includes electronics that, as known in the art, communicate signals to a corresponding monitor 135, which communicates electronically with a processing element 150, such as one or more microprocessors or microcontrollers, of a respiratory monitor 160. Flow meter 120, if present, may communicate signals to a corresponding monitor 125, as known in the art. Monitor 125 may, in turn, communicate electronically with processing element 150. Processing element 150 is programmed to determine an amount of at least one gas present in respiration of subject S based, at least in part, on signals communicated thereto from optical sensor 130, as known in the art.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An optical sensor, comprising:
a housing;
a radiation emitter disposed within the housing; and
an optical element through which the radiation is emitted, wherein the optical element comprises:
a base substrate including a material that is substantially transparent to a warming radiation; and
a warming coating that absorbs warming radiation operatively coupled to the base substrate such that heat absorbed by the warming coating is transferred to the base substrate thereby heating the base substrate.

2. The optical sensor of claim 1, wherein the optical element comprises a lens, a window, or both.

3. The optical element of claim 1, wherein the base substrate comprises silicon, calcium fluoride, magnesium fluoride, barium fluoride, germanium, potassium chloride, potassium bromide, zinc selenide, zinc sulfide, and magnesium fluoride, or any combination thereof.

4. The optical element of claim 3, wherein the warming coating comprises sapphire, borosilicate glass, crystal quartz, polycarbonate, a coating, a dopant, or any combination thereof.

5. The optical element of claim 3, wherein the warming coating is a dopant, and wherein the base substrate is doped with the dopant.

6. The optical element of claim 3, wherein the coating is disposed over at least a portion of a surface of the base substrate.

7. The optical element of claim 3, wherein the warming coating is disposed at only a portion of a region of the base substrate through which an optical path passes.

8. The optical element of claim 7, wherein the portion includes a plurality of discrete segments.

* * * * *